United States Patent [19]
Laske et al.

[11] Patent Number: 5,578,068
[45] Date of Patent: Nov. 26, 1996

[54] MEDICAL ELECTRICAL LEAD WITH RADIALLY ASYMMETRIC TIP

[75] Inventors: Timothy G. Laske, Shoreview; Gioi T. Tran, Eden Prairie, both of Minn.

[73] Assignee: Medtronic, Inc., Minneapolis, Minn.

[21] Appl. No.: 437,460

[22] Filed: May 8, 1995

[51] Int. Cl.⁶ .................................................. A61N 1/05
[52] U.S. Cl. .................................................. 607/126
[58] Field of Search ............................ 607/120–128; 128/642

[56] References Cited

U.S. PATENT DOCUMENTS

| | | |
|---|---|---|
| 4,409,994 | 10/1983 | Doring . |
| 4,502,492 | 3/1985 | Bornzin . |
| 4,519,404 | 3/1985 | Fleischhacker . |
| 4,957,118 | 9/1990 | Erlebacher ........................ 607/128 |
| 5,261,418 | 11/1993 | Ferek-Petric .................... 607/126 |

FOREIGN PATENT DOCUMENTS

| | | | |
|---|---|---|---|
| 2575925 | 7/1986 | France | 607/127 |

*Primary Examiner*—Jeffrey R. Jastrzab
*Attorney, Agent, or Firm*—Reed A. Duthler; Harold R. Patton

[57] ABSTRACT

A medical electrical lead with an elongated lead body containing an elongated conductor and carrying a tip electrode mounted to and extending the distal tip of the lead body, coupled to the conductor. The distal tip of the lead body includes flange portions extending radially outward from a point immediately adjacent to the electrode and flat portions extending longitudinally and proximally from the electrode. The flange portions and flat portions alternate around the circumference of the lead body tip.

7 Claims, 2 Drawing Sheets

5,578,068

MEDICAL ELECTRICAL LEAD WITH RADIALLY ASYMMETRIC TIP

FIELD OF THE INVENTION

This invention relates to the field of body implantable medical electrical leads, and in particular to transvenous pacing and defibrillation leads.

BACKGROUND OF THE INVENTION

Transvenous leads for cardiac pacing and defibrillation are well known to the art. Recently, in conjunction with the development of porous and steroid eluting electrodes, there has been a trend toward the use of smaller pacing electrodes, located on the tips of such leads. While the use of smaller electrodes is valuable in decreasing pacing thresholds, their smaller cross sectional areas proportionally increase the force per unit area applied by the electrodes to the tissue of the heart, if the cross sectional area of the lead is also correspondingly reduced. One method of avoiding this problem is to provide a tip sleeve immediately proximal to the electrode, which extends radially outward from the electrode and thereby increase the cross sectional area of the tip of the lead. One example of such a lead tip configuration may be found on the Medtronic Model 6968 ventricular pacing/defibrillation lead.

SUMMARY OF THE INVENTION

The present invention is directed toward an improvement to pacing and defibrillation leads as discussed above. In particular, a lead according to the present invention is provided with a modified lead tip configuration wherein the lead body immediately proximal to the electrode includes a first portion extending radially outward from a point adjacent the electrode and a second portion extending proximal from a point immediately adjacent the electrode and having a radial dimension no greater than the electrode. As a result of constructing the tip of the lead in this fashion, small proximal dislodgements of the electrode are less likely to result in the electrode losing contact with the heart tissue.

DETAILED DESCRIPTION OF A PREFERRED EMBODIMENT

FIG. 1 shows a side plan view of an endocardial pacing/defibrillation lead according to the present invention;

FIG. 2 shows a side view of the distal end of the lead shown in FIG. 1.

FIG. 3 shows a top view of the distal end of the lead shown in FIG. 1.

FIG. 4 shows a distal end view of the lead shown in FIG. 1.

Figure 1:
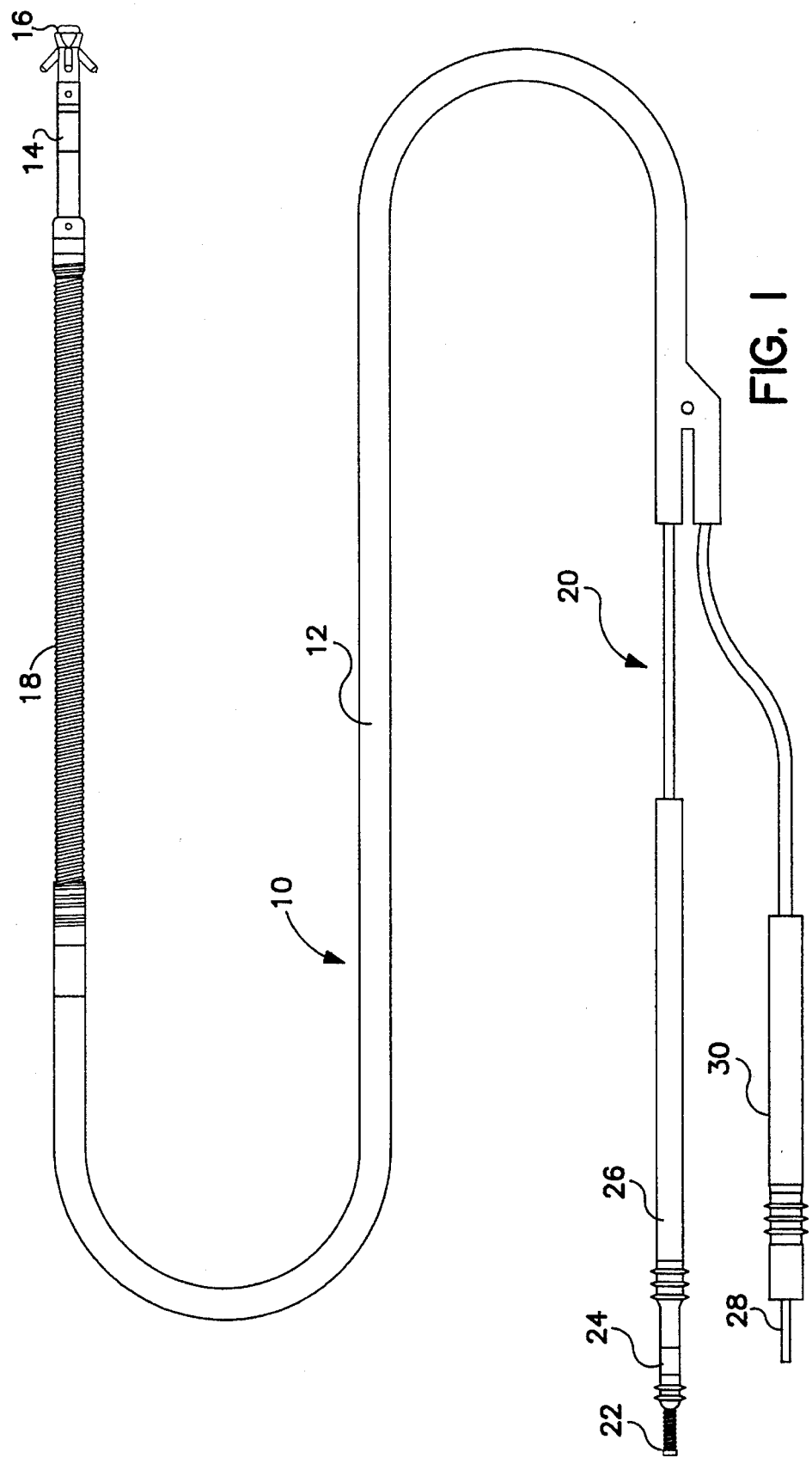
FIG. 1 is a plan view of a ventricular pacing/defibrillation lead embodying the present invention. The lead 10 includes an elongated insulative lead body 12, carrying three mutually insulated conductors. Located adjacent the distal end of the lead 10 are a ring electrode 14, a tip electrode 16, and an elongated coil defibrillation electrode 18. Each of the electrodes is coupled to one of the conductors within the lead body 12. Electrodes 14 and 16 are employed for cardiac pacing and for sensing ventricular depolarizations.

At the proximal end of the lead is a bifurcated connector assembly 20 which carries three electrical connectors, each coupled to one of the conductors. Connector pin 22 and connector ring 24 are located on an IS-1 type bipolar in-line connector 26. Pin 22 and ring 24 are coupled to electrodes 16 and 14, respectively by means of two of the three conductors within lead body 12. Connector pin 28 is located on a high voltage unipolar connector 30. Pin 28 is coupled to defibrillation electrode 18 by means of the third conductor within lead body 12.

Defibrillation electrode 20 may be fabricated from platinum, platinum alloy or other materials known to be usable in implantable defibrillation electrodes and may be about 5 cm in length. Ring electrode 14 may be fabricated of the same materials. Tip electrode 16 may be a porous, steroid eluting electrode as disclosed in U.S. Pat. No. 4,506,680 issued to Stokes and incorporated herein by reference in its entirety.

Figure 2:
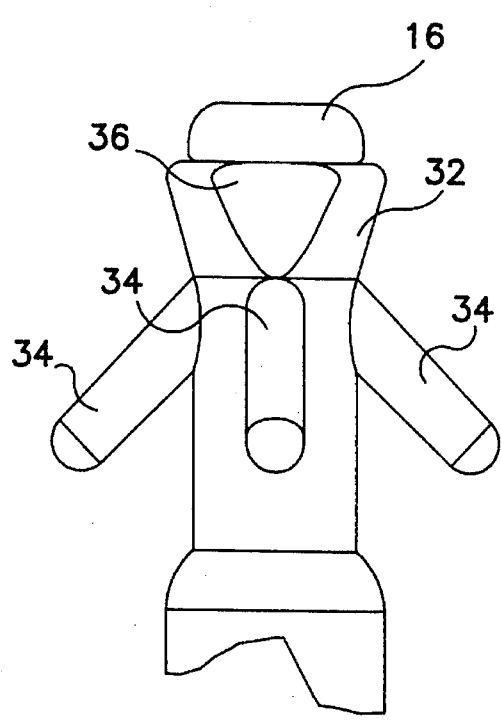

FIG. 2 illustrates a side plan view of the distal tip of the lead of FIG. 1. Electrode 16 is mounted at the distal end of a conductive shank, which, as disclosed in the above-cited Stokes patent contains a monolithic controlled release device (MCRD), loaded with asteroid drug such as sodium dexamethasone phosphate. As disclosed in the Stokes patent, the electrode 14 is provided with an internal elution path, allowing the steroid to exit at the distal tip of the electrode, and the electrode itself is either fabricated from porous sintered metal particles or provided with a coating thereof. However, the present invention may also be workably practiced with non-porous and/or non-drug eluting electrodes such as disclosed in U.S. Pat. No. 4,502,492 issued to Bornzin, U.S. Pat. No. 4,409,994, issued to Doring or U.S. Pat. No. 4,519,404, issued to Fleischacker, all incorporated herein by reference in their entireties, or with other endocardial electrode configurations.

Surrounding the electrode shank, located immediately proximal to electrode 14 is tine sleeve 32, which carries four pliant tines 34. Sleeve 32 may be fabricated of silicone rubber, polyurethane, or other biocompatible plastic. As can be seen in this view, sleeve 32 extends radially outward from electrode 14 immediately proximal to the electrode. Also visible in this view is one of two flattened areas 36, the central portion of which extends proximally, parallel to the lead axis, from a point immediately adjacent the proximal end of electrode 14.

Figure 3:
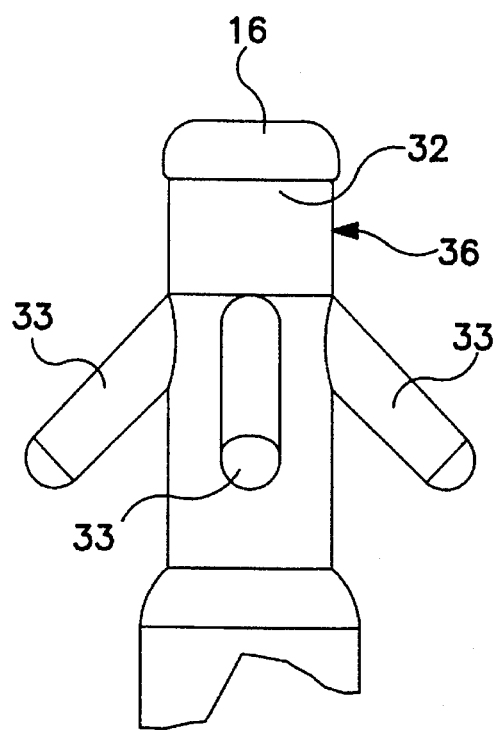
Figure 4:
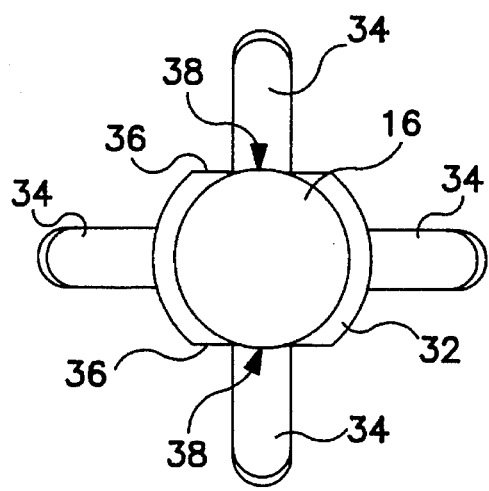

FIG. 3 illustrates a top view of the distal end of the lead illustrated in FIG. 1. All labeled elements thus correspond to those identically labeled in FIG. 2. FIG. 4 is an end view of the distal end of the lead illustrated in FIG. 1. All labeled elements thus correspond to those identically labeled in FIG. 2. In this view, it can be seen that flattened areas 36 define parallel, planar areas which have central portions 38 are either tangent to or located somewhat radially inward from the outer periphery of electrode 14.

The tip geometry illustrated in FIGS. 2–4 is believed beneficial in the context of a transvenous pacing or defibrillation lead, in that the portions of sleeve 32 which extend radially outward from electrode 14 provide flange sections which in turn effectively provide an increased tip surface area, reducing the force per unit area which the lead applies to the heart. Unlike prior designs employing sleeves which include flange portions which extend radially outward from the electrode around its complete circumference, the flattened areas 36 allow the electrode 14 to still define the outer periphery of the lead, around some portions of the circumference of the tip. This feature in turn is believed beneficial in reducing the effects of minor dislodgements of the lead in a proximal direction, for the reasons set forth below.

After an endocardial lead is implanted, the heart tissue generally comes to closely surround the tip of the lead. Thus, in a lead of the type a sleeve which extends radially outward from the electrode around its complete circumference, tissue located proximal to the electrode will be spaced radially outward from the electrode. A sight proximal dislodgement of the lead tip thus may pull the electrode out of direct contact with the heart tissue. However, in the case of a lead tip configured as in FIGS. 2–4, tissue adjacent the central portions of the flattened ares 36 will still be available for direct contact with the electrode 14, even if the lead is displaced slightly in a proximal direction.

Although the lead illustrated in FIGS. 2–4 is provided with two areas located radially inward of the outer periphery of the electrode, alternative designs having only one such area or having three or more such areas alternating with flange potions are also believed workable in the context of the present invention. Similarly, the portions located radially inward or tangent to the electrode need not be flat surfaces. For example a tip sleeve having an oval configuration in cross section might also be employed. Thus, the specific design illustrated in FIGS. 2–4 should be considered exemplary, rather than limiting, with respect to the claims which follow.

What is claimed is:

1. A medical electrical lead, comprising: an elongated lead body having a distal tip and containing an elongated conductor; and a tip electrode mounted to and extending from the distal tip of said lead body, coupled to the conductor, wherein the distal tip of said lead body includes a first portion defining a flange extending radially outward from a point immediately adjacent to said tip electrode and a second portion extending longitudinally and proximally from a point immediately adjacent said tip electrode and having a radial dimension no greater than said tip electrode, and wherein said second portion comprises multiple, generally planar surfaces extending proximally from said tip electrode.

2. A lead according to claim 1 wherein said generally planar surfaces are parallel to one another and located on opposite sides of the distal tip of said lead body.

3. A lead according to claim 1 wherein said first portion defines multiple flanges extending radially outward and wherein said flanges and generally planar surfaces alternate with one another circumferentially around the distal tip of said lead body.

4. A medical electrical lead, comprising: an elongated lead body having a distal tip and containing an elongated conductor; and a tip electrode mounted to and extending from the distal tip of the lead body, coupled to the conductor, wherein the distal tip of the lead body includes first portions defining flanges extending radially outward from points immediately adjacent to the electrode and second portions extending longitudinally and proximally from points immediately adjacent the electrode and having radial dimensions less than the electrode, the first and second portions alternating with one another circumferentially around the distal tip of said lead body.

5. A medical electrical lead, comprising: an elongated lead body having a distal tip and containing an elongated conductor; a tip electrode mounted to and extending from the distal tip of the lead body, coupled to the conductor; and a plurality of tines mounted extending outward from the lead body at points spaced proximally from the tip electrode, wherein the distal tip of the lead body includes first portions defining flanges extending radially outward from points immediately adjacent to the electrode and second portions extending longitudinally and proximally from points immediately adjacent the electrode and having a radial dimension no greater than the electrode, the first and second portions alternating with one another circumferentially around the distal tip of said lead body.

6. A lead according to claim 5 wherein the second portions extend between the tip electrode and the tines.

7. A lead according to claim 4 or claim 5 or claim 6 wherein the second portions are generally planar surfaces extending proximally from the tip electrode.

* * * * *